US008998828B2

(12) United States Patent
Reichow et al.

(10) Patent No.: US 8,998,828 B2
(45) Date of Patent: Apr. 7, 2015

(54) VISUALIZATION TESTING AND/OR TRAINING

(75) Inventors: Alan W. Reichow, Beaverton, OR (US); Herb Yoo, Beaverton, OR (US)

(73) Assignee: NIKE, Inc., Beaverton, OR (US)

(*) Notice: Subject to any disclaimer, the term of this patent is extended or adjusted under 35 U.S.C. 154(b) by 509 days.

(21) Appl. No.: 12/500,385

(22) Filed: Jul. 9, 2009

(65) Prior Publication Data

US 2011/0009777 A1    Jan. 13, 2011

(51) Int. Cl.
*A61B 3/032* (2006.01)
*A61B 5/103* (2006.01)
*A61B 5/117* (2006.01)
(Continued)

(52) U.S. Cl.
CPC .............. *A61B 3/032* (2013.01); *A61B 3/113* (2013.01); *A61B 5/0402* (2013.01); *A61B 5/0476* (2013.01); *A61B 5/0496* (2013.01); *A61B 5/1036* (2013.01); *A61B 5/1127* (2013.01); *A63B 23/025* (2013.01); *A63B 24/0006* (2013.01); *A63B 26/003* (2013.01); *A63B 69/0053* (2013.01); *A63B 71/0622* (2013.01); *A63B 2024/0015* (2013.01); *A63B 2071/0666* (2013.01); *A63B 2220/40* (2013.01); *A63B 2220/52* (2013.01); *A63B 2220/56* (2013.01); *A63B 2220/803* (2013.01); *A63B 2220/806* (2013.01); *A63B 2230/00* (2013.01); *A63B 2230/06* (2013.01); *A63B 2230/30* (2013.01); *A63B 2230/40* (2013.01); *A63B 2230/62* (2013.01)

(58) Field of Classification Search
CPC .... A61B 3/032; A61B 5/1036; A61B 5/1127; A61B 23/025; A61B 24/0006; A61B 71/0622

USPC .......................................... 600/558, 587, 595
See application file for complete search history.

(56) References Cited

U.S. PATENT DOCUMENTS

| | | | |
|---|---|---|---|
| 3,861,790 | A | 1/1975 | Tamura |
| 4,869,589 | A | 9/1989 | Blair et al. |

(Continued)

FOREIGN PATENT DOCUMENTS

| | | | |
|---|---|---|---|
| JP | H024309 A | 1/1990 | |
| JP | 6217938 | 8/1994 | |

(Continued)

OTHER PUBLICATIONS

International Search Report and Written Opinion for PCT/US08/60229; Sep. 9, 2008.

(Continued)

*Primary Examiner* — Adam Eiseman
(74) *Attorney, Agent, or Firm* — Shook, Hardy & Bacon L.L.P.

(57) ABSTRACT

The visual and/or visualization skills of a subject may be tested and/or trained using systems and methods in accordance with the present invention. Visual stimuli may be presented to a test subject. Measurements relating to the performance of the subject, such as stability information, eye movement data, physiological information, or other information, may be made both with and without visual stimuli being provided to a subject. Similar measurements may be made while the subject visualizes the visual stimuli, and the collected data may be compared to evaluate the subject's ability to visualize visual stimuli. Secondary stimuli may also be provided to subject as part of this process, or mental activities may be required by subject as well.

23 Claims, 7 Drawing Sheets

(51) Int. Cl.
*A61B 5/11* (2006.01)
*A63B 23/025* (2006.01)
*A63B 24/00* (2006.01)
*A63B 71/06* (2006.01)
*A61B 3/113* (2006.01)
*A61B 5/0402* (2006.01)
*A61B 5/0476* (2006.01)
*A61B 5/0496* (2006.01)
*A63B 26/00* (2006.01)
*A63B 69/00* (2006.01)

(56) References Cited

U.S. PATENT DOCUMENTS

| | | | |
|---|---|---|---|
| 5,050,982 | A | 9/1991 | Meissner |
| 5,088,810 | A | 2/1992 | Galanter |
| 5,478,239 | A | 12/1995 | Fuerst |
| 5,520,393 | A | 5/1996 | Rickey, Jr. |
| 5,812,239 | A | 9/1998 | Eger |
| 5,825,460 | A | 10/1998 | Kohayakawa |
| 5,919,149 | A * | 7/1999 | Allum ............ 600/595 |
| 6,092,058 | A | 7/2000 | Smyth |
| 6,261,239 | B1 | 7/2001 | Abraham-Fuchs |
| 6,267,733 | B1 * | 7/2001 | Peterson et al. ......... 600/587 |
| 6,364,845 | B1 | 4/2002 | Duffy |
| 6,430,997 | B1 | 8/2002 | French et al. |
| 6,632,174 | B1 | 10/2003 | Breznitz |
| 6,755,525 | B2 | 6/2004 | Reichow |
| 6,796,927 | B2 | 9/2004 | Toyama |
| 6,811,258 | B1 | 11/2004 | Grant |
| 6,893,127 | B2 | 5/2005 | Reichow |
| 7,073,208 | B2 | 7/2006 | Penque |
| 7,326,060 | B2 | 2/2008 | Seiller et al. |
| 7,849,115 | B2 | 12/2010 | Reiner |
| 8,240,851 | B2 | 8/2012 | Reichow et al. |
| 8,513,055 | B2 | 8/2013 | Reichow et al. |
| 2003/0120183 | A1 | 6/2003 | Simmons |
| 2003/0211449 | A1 | 11/2003 | Seiller |
| 2004/0141152 | A1 | 7/2004 | Marino |
| 2004/0167380 | A1 | 8/2004 | Simon |
| 2005/0053904 | A1 | 3/2005 | Shepard |
| 2005/0273017 | A1 | 12/2005 | Gordon |
| 2006/0161218 | A1* | 7/2006 | Danilov ............ 607/45 |
| 2006/0194178 | A1 | 8/2006 | Goldstein |
| 2006/0195018 | A1 | 8/2006 | Guillen |
| 2006/0244915 | A1 | 11/2006 | Clemons |
| 2006/0251334 | A1* | 11/2006 | Oba et al. ........... 382/275 |
| 2006/0287617 | A1 | 12/2006 | Taub |
| 2007/0013870 | A1 | 1/2007 | Hara et al. |
| 2007/0052674 | A1 | 3/2007 | Culver |
| 2007/0179534 | A1 | 8/2007 | Firlik et al. |
| 2007/0184953 | A1* | 8/2007 | Luberski et al. ........ 482/146 |
| 2007/0254270 | A1 | 11/2007 | Hersh |
| 2008/0003553 | A1 | 1/2008 | Stark |
| 2008/0189173 | A1 | 8/2008 | Bakar et al. |
| 2009/0093305 | A1* | 4/2009 | Okamoto et al. ........ 463/36 |

FOREIGN PATENT DOCUMENTS

| | | |
|---|---|---|
| JP | 6237895 | 8/1994 |
| JP | H07-005679 | 1/1995 |
| JP | 7299033 | 11/1995 |
| JP | 10305016 | 11/1998 |
| JP | H 11225961 | 2/1999 |
| JP | 11267101 | 10/1999 |
| JP | 11318824 | 11/1999 |
| JP | 2003102868 | 4/2003 |
| JP | 2003126036 | 5/2003 |
| JP | 2003126291 | 5/2003 |
| JP | 2004135756 | 5/2004 |
| JP | 2004528953 | 9/2004 |
| JP | 2004329795 A | 11/2004 |
| WO | 9802083 A2 | 1/1998 |
| WO | 02102469 | 12/2002 |
| WO | 2004006747 | 1/2004 |
| WO | 2006029048 | 3/2006 |
| WO | 2006088415 | 8/2006 |
| WO | 2007000990 | 1/2007 |
| WO | 2008128183 A1 | 10/2008 |

OTHER PUBLICATIONS

Supplemental European Search Report for EPO08745763; Jun. 16, 2010.
International Search Report and Written Opinion for PCT/US08/602349; Sep. 8, 2008.
Herdman, et al., "Computerized Dynamic Visual Acuity Test in the Assessment of Vestibular Deficits", The American Journal of Otology, 1998, pp. 790-796, vol. 19, No. 6, United States.
Supplemental European Search Report for EPO08745783; Jun. 23, 2010.
International Search Report and Written Opinion for PCT/US08/60244; Sep. 4, 2008.
Supplemental European Search Report for EPO08745778.4;Jun. 23, 2010.
Supplemental European Search Report for EPO08780526;Jun. 16, 2010.
International Search Report and Written Opinion for PCT/US08/60252; Aug. 15, 2008.
International Search Report and Written Opinion for PCT/US09/043127; Jul. 6, 2009.
Office Action of Apr. 6, 2011; U.S. Appl. No. 12/595,209.
Office Action of Jan. 6, 2011; U.S. Appl. No. 12/117,315.
Final Office Action of May 26, 2011; U.S. Appl. No. 12/117,315.
Office Action of Jul. 12, 2011; U.S. Appl. No. 12/595,209.
Reichow, et al, "Introduction to Behavioral Optometry", Sports Vision, 1993, 75 pages, Optometric Extension Program Foundation, United States.
Ferreira, "An Overview of Research in Sports Vision: its History and an Optometric Perspective", The South African Optometrist, Dec. 2003, pp. 142-149, vol. 62, No. 4, Auckland Park, South Africa.
Coffey, et al., "Visual Performance Enhancement in Sports Optometry", Sports Vision 1995, pp. 158-177, Butterworth-Heinermann, United States.
Cardall, "Contact Lenses in Sport: a General Overview", Optician, Jan. 13, 2006, pp. 22-25, vol. 231, No. 6034, United States.
Rouse, et al., "A Comparison Study of Dynamic Visual Acuity Between Athletes and Nonathletes", Journal of the American Optometric Association, Dec. 1988, pp. 946-950, vol. 59, No. 12, United States.
Koenig, "Practicing Perception: Eyes Can Be Trained to be More Effective", USA Today Baseball Weekly, 1996, 3 pages, United States.
Coffey, et al., "Optometric Evaluation of the Elite Athlete," Problems in Optometry, Mar. 1990, pp. 32-59, vol. 2, No. 1, United States.
Reichow, et al., "A Comparison of Contrast Sensitivity in Elite Athletes Versus a Normal Population", American Journal of Optometry and Physiological Optics, Dec. 15, 1986, vol. 63, No. 82, United States.
Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.
Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.
Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.
Final Office Action in U.S. Appl. No. 12/595,209 mailed Jan. 13, 2012, 17 pages.
Notice of Allowance and Fees Due in U.S. Appl. No. 12/595,207 mailed Apr. 12, 2012, 79 pages.
Final Office Action in U.S. Appl. No. 12/595,208 mailed May 10, 2012, 25 pages.

(56) References Cited

OTHER PUBLICATIONS

Non-Final Office Action in U.S. Appl. No. 12/595,209 mailed Jul. 13, 2012, 32 pages.
Final Office Action in U.S. Appl. No. 12/595,209, mailed Feb. 6, 2013, 35 pages.
Notice of Allowance and Fees Due in U.S. Appl. No. 13/584,454, mailed Apr. 7, 2014, 21 pages.
Office Action in U.S. Appl. No. 12/595,207 mailed Nov. 10, 2011, 19 pages.
Office Action in U.S. Appl. No. 12/595,208 mailed Nov. 28, 2011, 20 pages.
A. Ludeke, et al., "The difference in visual skills between professional versus non-professional rugby players" The South African Optometrist, Dec. 1, 2003 pp. 150-158, XP055044423.
Martjin LTM Muller:"Attentional components of postural control" Dissertation, 2007, XP055044427, Saline MI (USA) Retrieved from the Internet: URL: http://dare.uva.n./document/48212 [retrieved on Nov. 15, 2012].
Kathryn W. O'Connor et al.: "Postural adaptations to repeated optic flow stimulation in older adults", Gait & Posture, vol. 28, No. 3, Mar. 10, 2008, pp. 385-391. Retrieved from the Internet Sep. 9, 2014: URL:http://www.ncbi.nlm.nih.gov/pmc/articles/PMC2605319/.
Mark S Redfern et al.: "Attention influences sensory integration for postural control in older adults", Gait & Posture, vol. 14, No. 3, Dec. 1, 2001, pp. 211-216.
European Search Report dated Sep. 26, 2014 in Application No. 10797929.6, 13 pages.
Non-Final Office Action dated Oct. 31, 2014 in U.S. Appl. No. 12/117,315, 9 pages.
Official Guidebook by Nintendo, "Rhythm Heaven", Shogajujan, Inc., Nov. 1, 2006, pp. 4, 5, 14, 15, 26, 27, 28, 29.
Kazutaka Toyoomi, Nintendo has improved "Visual Ability" through a simple training. DS software: "DS Visual Ability Training for Improving Ability to See through Actual Practice" GAME Watch, May 18, 2007, http://game.watch.impress.co.jp/docs/20070518/meji.htm.
Shigenori Agura, "Sports Vision", Science for Children, October issue, Sep. 17, 2002, vol. 65 (10), pp. 10-18.
Final Office Action in U.S. Appl. No. 13/584,454, mailed Dec. 24, 2013, 25 pages.
Final Office Action dated Jun. 26, 2014 in U.S. Appl. No. 12/595,210, 14 pages.
Non-Final Office Action dated Sep. 11, 2014 in U.S. Appl. No. 12/117,315, 10 pages.
Non Final Office Action in U.S. Appl. No. 12/595,210. mailed Sep. 3, 2013, 78 pages.
Non-Final Office Action in U.S. Appl. No. 13/584,454 mailed Apr. 11, 2013, 35 pages.

* cited by examiner

VISUALIZATION TESTING AND/OR TRAINING

CROSS-REFERENCE TO RELATED APPLICATIONS

This application is a continuation-in-part of PCT Application No. 2008/60229, entitled "Unitary Vision Testing Center," and filed on Apr. 14, 2008, which claimed priority to U.S. Provisional Application No. 60/923,434, entitled "System and Method for Testing Visual Ability During Simulated Activity" and filed on Apr. 13, 2007, and which also claimed priority to U.S. Provisional Application No. 60/941,915, entitled "System and Method for Decoupled Visual Ability Testing" and filed on Jun. 4, 2007.

STATEMENT REGARDING FEDERALLY SPONSORED RESEARCH OR DEVELOPMENT

Not applicable.

TECHNICAL FIELD

The present invention relates to vision testing. More particularly, the present invention relates to testing and training an individual's abilities to perceive and visualize visual stimuli.

BACKGROUND OF THE INVENTION

Visual abilities are obviously important for those who engage in almost any activity. One particular example of activities that place demands upon an individual's visual skills are sports and athletics. All other things being equal, an athlete with strong visual skills will possess an advantage over an athlete with less strong visual skills. In addition to the simple ability to see objects clearly using the physical structures of the eye, however, the neurological capabilities relating to visual performance are also important to an athlete engaging in a sport, or any individual engaging in activities requiring visual processing.

The concept of "visualization" has gained some acceptance in athletic training. For example, athletes are encouraged to image or "visualize" certain scenarios as part of preparing to compete. A quarterback in the game of American football might be asked to visualize defenses he is likely to encounter during a game; a soccer goal keeper might be asked to visualize saving penalty kicks; a basketball player might be asked to visualize shooting free throws with a game on the line. While the use of such visualization is often credited with helping individual athletes prepare for competition, athletes, coaches, trainers, and others have not been able to objectively assess the capabilities of an athlete engaging in visualization.

SUMMARY OF THE INVENTION

The present invention generally relates to the testing and/or training of the visual and visualization abilities of an athlete or other individual. More particularly, the present invention measures the objective performance of a subject when presented with visual stimuli and compares that performance to the subject's performance when visualizing the visual stimuli. The performance of a subject may also be measured in the absence of visual stimuli and without visualizing visual stimuli, which may provide a baseline for comparison. In this way, the individual subject's visualization abilities may be measured objectively and courses may be suggested to improve the subject's visualization abilities. By making the visualization abilities of a given individual objectively assessable, establishing a baseline and training an individual to better or more effectively visualize as part of training and/or preparation is greatly improved. Systems and methods in accordance with the present invention may also identify deficiencies in the vision of a subject that may prevent the subject from effectively visualizing a given visual stimuli. Systems and methods in accordance with the present invention may be utilized to both test and train a subject's visualization capabilities.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

Figure 2:
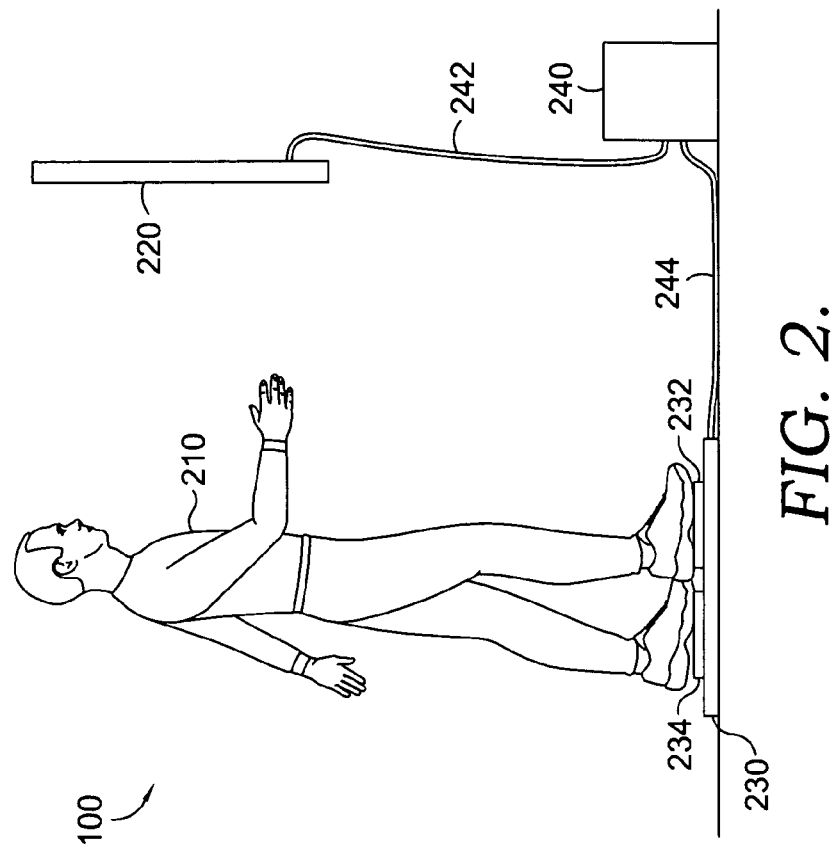
FIG. 2 illustrates a further system the visualization abilities in accordance with the present invention.

The present invention provides systems and methods for testing and/or training a subject's vision and visualization abilities. Systems and methods in accordance with the present invention may measure the subject's performance with visual stimuli presented, with no visual stimuli presented, and/or while the subject is visualizing the visual stimuli. Comparing the data collected with visual stimuli presented to the data collected, with no visual stimuli presented and/or to the data collected while the subject visualizes visual stimuli may be used to evaluate a subject's ability and/or to train the individual. Systems and methods in accordance with the present invention may also store the collected data, store representations of the collected data, output graphical or numerical representations of the collected data, compare the collected data to other collected data, and/or output graphical or numerical representations of the comparison of the collected data. The visualization in which a subject engages may be projective (i.e., the subject sees an image), manipulative (i.e., the subject interacts with the image), or a combination of projective and manipulative visualization. A comparison of data taken during projective and manipulative imagery may also be made.

Visual stimuli used with the present invention may range from the simple to the complex and from the static to the dynamic. For example, a simple dot or light, either stationary or moving, may be used as a visual stimuli. Slightly more complex stimuli, such as letters, numerals, arrows, Landolt Cs, and the like may also be used (either stationary or moving). Complex visual stimuli, such as recorded-video sequences of an activity or computer animation of an activity, may also be used. Virtual reality technology may be used to present visual stimuli to a subject. Non-visual stimuli, such as sounds, may also, be provided to a subject. Further visual stimuli may be presented using two dimensional and/or three dimensional display devices. For example, the visual stimuli presented to an individual may represent visual stimuli typically encountered in the sport/activity of interest to the subject within the visual context of the activity, such as a baseball as it is pitched. Visual stimuli used in accordance with the present invention may be simpler or more complex than the examples described herein.

Generally speaking, the performance data collected from an individual accurately visualizing visual stimuli may be expected to match the performance data collected from an individual while the individual is being exposed to that stimuli. For example, an individual would likely experience a similar physiological response both to being presented visual stimuli depicting a football play and to visualizing the same football play. Physiological data may be collected from an individual in each instance, and differences in the physiological data between these two instances might indicate that some aspect of the play is not being visualized accurately. Similarly, the lack of differences in a physiological response, as indicated by collected physiological data, when a subject is exposed to visual stimuli as compared to when a subject is not exposed to visual stimuli could indicate that the subject has experienced difficulty perceiving the visual stimuli. Performance data collected in accordance with the present may be of any type, including physiological data, stability data, and/or eye movement data. Of course, the appropriate analysis of collected performance data may vary based upon a variety of factors, such as what type of performance data is collected and what visual stimuli is presented and/or visualized.

One type of performance data that may be collected using systems and methods in accordance with the present invention is stability data relating to an individual. Stability data may describe an individual's balance and may be collected in a wide variety of ways. For example, pressure plates, inertial sensors, motion detectors, or other types of equipment may be used to measure a subject's balance, stability, movement, and/or weight distribution during testing and/or training. One example of systems and methods that may be used to collect stability data are shoes having sensors such as those disclosed in Provisional Patent Application No. 61/061,427 entitled "Footwear Having Sensor System and Universal Communication Port" and/or Patent Application No. 61/138,048 entitled "Foot Gestures for Computer Input and Interface Control." Other types of performance data that may be collected in addition to, or instead of, stability data includes physiological data such as blood pressure, respiration rate, heart rate, perspiration rate, EEG (electroencephalography) and EKG (electrocardiogram) data, and other types of physiological data. Other types of performance data, such as inputs using input devices such as buttons, gesture recognition, voice recognition, joysticks, touch sensitive screens and the like may also be collected, for example in response to a displayed visual stimuli. Performance data collected in accordance with the present invention may alternatively or additionally be eye movement data. Performance data collected in accordance with the present invention may alternatively or additionally be eye movement data. The collection of eye movement data in conjunction with stability data may be used to ascertain whether an individual's equilibrium suffers during particular eye movements. Eye movement data, if collected, may be collected in any way. The use of an electrooculogram (EOG) to monitor eye movement may be particularly advantageous, as the use of an EOG can provide eye movement data during visualization by a subject if the subject closes her/his eyes.

Figure 1:
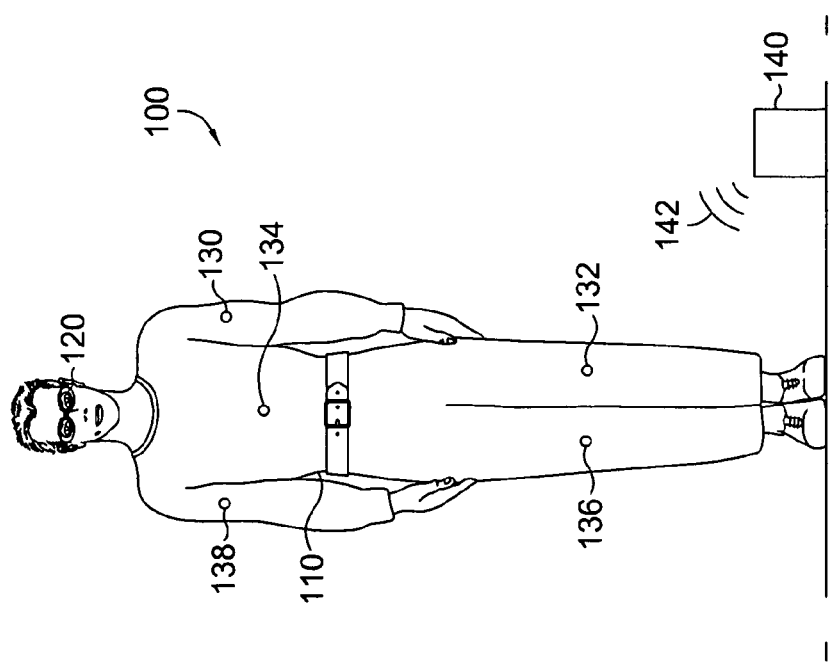
FIG. 1 illustrates a system for testing and/or training visualization abilities in accordance with the present invention.

Referring now to FIG. 1, a system 100 in accordance with the present invention is illustrated. System 100 may be used for testing and/or training visual and/or visualization abilities of subject 110. System 100 may include a display device such as visual goggles 120 to provide visual stimuli to subject 110. Other types of display devices, such as monitors and/or projection screens, or any other device capable of outputting visual stimuli in either two or three dimensions may be used, either in place of goggles 120 or in addition to goggles 120. Performance data regarding the performance of subject 110 may be measured by one or more stability detection devices, such as inertial sensors 130, 132, 134, 136, 138 that may be affixed to subject 110 or the clothes of subject 110. A control unit 140 may comprise any type of computing device executing software causing it to operate in accordance with the present invention. Control unit 140 may provide the visual stimuli to goggles 120 and receive data measurements from sensors 130, 132, 134, 136, 138. Optionally, goggles 120 may include eye movement monitoring equipment (not illustrated) that may also provide data measurements to control unit 140. Control unit 140 may communicate with other components of system 100 via a wireless link 142, although wires, cables, or any other types of connections may be utilized as an alternative and/or as an addition to wireless link 142. Control unit 140 may provide visual stimuli for display on goggles 120 and record measurements from inertial sensors 130, 132, 134, 136, 138 while the visual stimuli is displayed to subject 110. Similarly, control unit 140 may receive data from inertial sensors 130, 132, 134, 136, 138 when subject 110 is not exposed to visual stimuli using goggles 120. Subject 110 may also engage in visualization of the stimuli that was displayed on goggles 120, with data collected from sensors 130, 132, 134, 136, 138 and recorded by control unit 140. During visualization of stimuli, control unit 140 may cause goggles 120 to become substantially opaque, which may reduce undesired or inadvertent visual stimuli perceived by subject 100. Alternatively, during visualization of stimuli control unit 140 may cause goggles 120 to display visual stimuli to increase the difficulty of visualization for subject 110. The data may then be compared to determine to what degree subject 110 behaves similarly both when actually exposed to a visual stimuli using goggles 120 and when subject 110 merely visualizes the stimuli, although other types of analysis may alternatively or additionally be performed on the collected stability data. The collected data may be stored, either on control unit 140 or at a remote location (not shown). Similarly, the comparison of the collected data may be stored, either on control unit 140 or at a remote location (not shown) Likewise, the comparison of collected data may occur at a remote location (not shown). A remote location may be accessed by control unit 140 via any type of network, no matter what protocol or media may be used. The remote location may comprise a server, storage device, or the like. Further, the collected data and/or the comparison of the collected data may be output, for example in a numerical and/or graphical form, to an output device (not shown). An output device may comprise, for example, a display, a printer, a display device such as goggles 120, or any other type of device that renders representations of data perceivable by individuals. A trainer, coach, medical professional, or other individual(s) assisting in the testing and/or training of subject 110 and or subject 110 himself/herself may utilize the representations of the collected data and/or comparisons of the collected data as part of the testing and/or training of the visual and/or visualization abilities of subject 110. One skilled in the art will appreciate that the process described in conjunction with system 100 may occur in various orders and may be repeated any number of times without departing form the scope of the present invention.

Referring now to FIG. 2, a further system 200 in accordance with the present invention is illustrated. Subject 210 may utilize system 200 to test and/or train his or her visual and/or visualization abilities. System 200 may include any number of data collection devices to collect performance data. Data collection devices may include stability measurement devices, physiological data collection devices, eye movement data collection devices, user operable input devices and other types of data collection devices, such as described herein. For example, subject 210 may stand upon platform 230 with the feet of subject 210 placed upon a first pressure sensitive plate 232 and a second pressure sensitive plate 234. Platform 230, first pressure sensitive plate 232, and second pressure sensitive plate 234 may operate, individually or in conjunction with one another, as a data collection device to measure the weight distribution and/or other stability data of subject 210. A display device, such as monitor 220, may present visual stimuli to subject 210. Display device may also comprise, for example, a screen upon which stimuli may be projected, a light source or plurality of light sources, display goggles (as illustrated in FIG. 1), any number of display devices used in combination, or any other device capable of providing visual stimuli to subject 210. Control unit 240 may comprise any sort of computing device executing software causing it to operate in accordance with the present invention. Control unit 240 may operate to control visual stimuli displayed on monitor 220 and to receive data from data collection devices, such as stability data from platform 230, first pressure sensitive plate 232, and/or second pressure sensitive plate 234. Control unit 240 may connect to monitor 220 via cable 242 and to platform 230, first pressure sensitive plate 232, and second pressure sensitive plate 234 via cable 244, although more or fewer cables may be used. One of ordinary skill in the art will also appreciate that cable 242 and/or cable 244 may be replaced with one or more alternative connections, such as wireless connections, and that test unit 240 may connect to other equipment of system 200 via any sort of cable, wire, wireless link, or other type of connection or communication methodology. Control unit 240 may operate to record stability data for subject 210 received from platform 230, first pressure sensitive plate 232, and/or second pressure sensitive plate 234 while test unit 240 causes no visual stimuli to be displayed on monitor 220. Test unit 240 may further record stability data for subject 210 received from platform 230, first pressure sensitive plate 232, and second pressure sensitive plate 234 while test unit 240 causes one or more visual stimuli to be displayed on monitor 220. Test unit 240 may also collect stability data of subject 210 from platform 230, first pressure sensitive plate 232, and second pressure sensitive plate 234 while subject 210 visualizes one or more visual stimuli, such as visual stimuli that have been previously displayed on monitor 220. During visualization of stimuli, control unit 240 may cause monitor 220 to become blank, which may reduce visual stimuli perceived by subject 210. Alternatively, during visualization of stimuli control unit 240 may cause monitor 220 to display visual stimuli to increase the difficulty of visualization for subject 210. One skilled in the art will appreciate that the processes described in conjunction with system 200 may occur in various orders and may be repeated any number of times without departing from the scope of the present invention.

Figure 3:
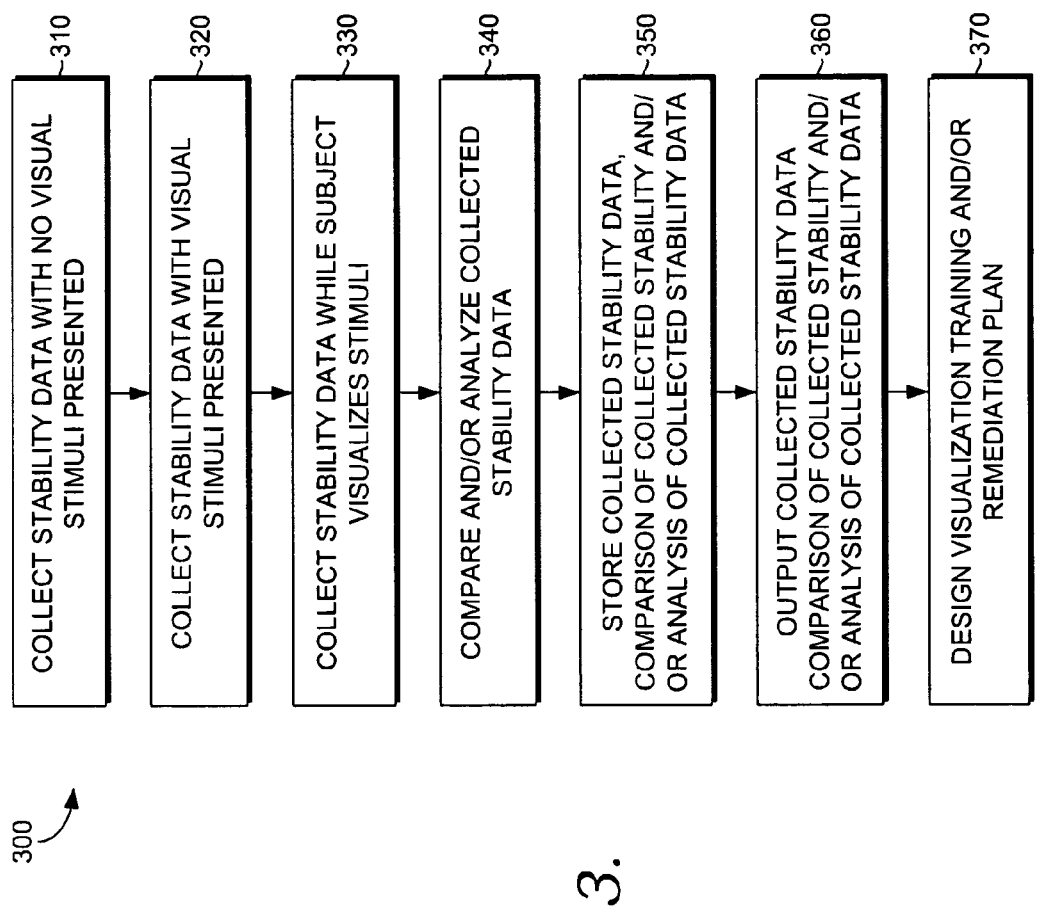
FIG. 3 illustrates a method for testing and/or training the visualization abilities of an individual in accordance with the present invention.

Referring now to FIG. 3, a method 300 for testing and/or training the visualization abilities of an individual in accordance with the present invention is illustrated. The steps of method 300 may be performed in orders different than those described herein and illustrated in FIG. 3, and the steps of method 300 may be repeated varying numbers of times or even omitted. In step 310, stability data may be collected with no visual stimuli presented to a subject for a period of time. In step 320, stability data may be collected while visual stimuli are presented to a subject for a period of time and without the individual imaging a visual stimuli. Data collected in step 310 may be used as a baseline, as it represents a measure of the stability of an individual with no presented visual stimuli and with no imaging performed. Optionally, an individual may be asked to mentally clear her/his mind, or exercises (such as spelling one's name backwards) may be performed by the subject to clear her/his mind of prior thought processes, images, etc. In step 330, stability data may be collected while the subject visualizes the visual stimuli for a period of time. In step 330, visual stimuli may be presented to subject, for example to increase the difficulty of visualization for subject, or, alternatively, no visual stimuli may be presented to subject to avoid distracting subject from visualization. If steps of collecting stability data with visual stimuli presented are followed by steps of collecting stability data with no visual stimuli presented, or vice versa, the visual stimuli may be prevented and/or removed gradually so as to avoid a startle reflex reaction from the subject, or suddenly, so as to increase the difficulty of training and/or testing for the subject. Method 300 may additionally/alternatively utilize delays between data collection in step 310, step 320, and/or step 330 to, for example, avoid collecting data from the subject during transitory periods.

The stability data collected in steps 310, 320, and 330 may be collected with any kind of sensor or system, including those described herein. The collected stability data may be compared in step 340. The comparison of step 340 may indicate, for example, that a subject's stability data taken in step 330 while subject is to visualize visual stimuli more closely resembles the stability data collected in step 310 with no visual stimuli presented than it does the stability data collected in step 320 when visual stimuli was presented. This discrepancy could indicate that the subject is encountering difficulty in the visualization process. In such a case, additional visualization practice, perhaps with easier visual stimuli or involving scenarios more familiar to the subject, could be pursued. By way of further example, the data collected in all of steps 310, 320, and 330 may be similar, which could indicate that the subject encountered difficulty visually perceiving the stimuli in the first instance and, therefor, also encounters difficulty in accurately visualizing the visual stimuli. In this case, a further investigation could be made to determine whether the subject could benefit from vision correction approaches, such as vision correction devices and/or vision exercises.

In step 350 the stability data collected in steps 310, 320, and/or 330 and/or the comparison of stability data from step 340 may be stored. The storing of step 350 may utilize any type of storage media, such as hard drives, flash memory, compact discs, dvds, floppy discs, tapes, and any other type of media. The storing of step 350 may occur on a control unit or at another location, such as a remotely located server. In step 360 the stability data collected in steps 310, 320, and/or 330 and/or the comparison of stability data from step 340 may be output to an output device. An output device used in conjunction with step 350 may comprise, for example, a display, a printer, a display device used to present visual stimuli to the subject, or any other type of device that can render a representation of data perceivable by an individual.

In step 370 a visualization training plan and/or remediation may be designed. Step 370 may utilize the stability data collected in steps 310, 320, and/or 330 and/or the comparison of stability data from step 340, as stored in step 350 or as output in step 360. Step 370 may be performed by a trainer, a coach, a medical profession, another individual(s) assisting in the testing and/or training of the individual, or the individual subject himself/herself. Further, step 370 may be performed, in whole or in part, by a computing device utilizing the data stored in step 350 and/or output in step 360. A computing device used in conjunction with step 370 may be integral to or separate from a control unit as described herein. A visualization training plan prepared in step 370 may include devices and/or training to improve a subject's visual ability, as an individual cannot visualize stimuli that he or she cannot accurately perceive in the first instance. A visualization training plan prepared in step 370 may also include visualization exercises of increasing complexity and/or difficulty.

Figure 4:
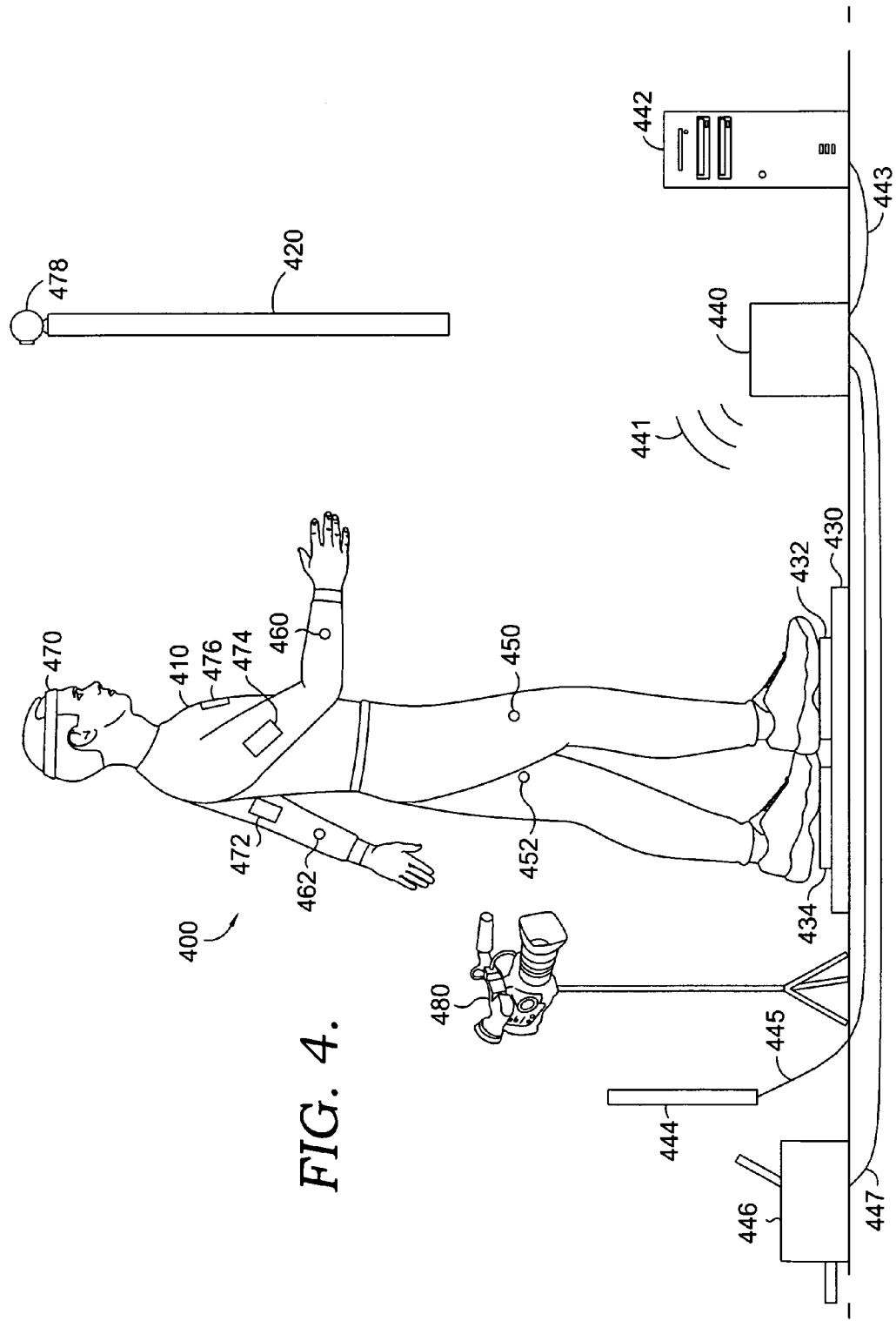
FIG. 4 illustrates a further system for testing and/or training the visualization abilities of an individual in accordance with the present invention.

Referring now to FIG. 4, a further system 400 in accordance with the present invention is illustrated. System 400 may be used by subject 410 to test and/or train his or her visual and/or visualization abilities. System 400 illustrates some of the various types of data collection devices that may be used to measure the behavior and/or responses of subject 410, although the data collection devices illustrated in FIG. 4 is in no way intended to be exhaustive of all data collection devices that may be used in systems and methods in accordance with the present invention. Platform 430, first pressure sensitive plate 432, and second pressure sensitive plate 434 may be used as data collection devices to record stability data as discussed previously with regard to FIG. 2. Similarly, first inertial sensor 450 and second inertial sensor 452 may be used as data collection devices to collect stability data as discussed above with regarding to FIG. 1.

As illustrated in FIG. 4, additional data may be collected using additional data collection devices of system 400 in addition to the data collection devices illustrated and discussed with regard to FIG. 1 and FIG. 2 above. For example, motion sensitive markers, such as first motion sensitive marker 460 and second motion sensitive marker 462, may be used in conjunction with motion detecting camera 480 to detect and record motion patterns of subject 410 or parts of subject 410. The brain activity of subject 410 may be measured using an EEG detector 470 or similar device. While not illustrated, other devices and methodologies for measuring brain activity, such as PET (positron emission tomography) scans, may be utilized. A blood pressure monitor 472 may measure the blood pressure of subject 410 and/or optionally, the heart rate of subject 410. Perspiration monitor 474 may record data regarding the perspiration rate and type of subject 410. EKG detector 476 may collect data regarding the function of the heart and circulatory system of subject 410. Eye movement monitor 478 may record movements of the eyes of subject 410, for example to determine whether they are tracking a visual stimulus displayed on monitor 420. While eye movement monitor 478 is illustrated at a distance from subject 410, any type of eye movement monitor, including an EOG or a monitor mounted on an eye glasses frame and/or a goggle display device, may be used in accordance with the present invention. Of course, other data collection devices beyond those described herein may be used without departing from the scope of the present invention.

FIG. 4 further illustrates monitor 420 that may be used as a display device to display visual stimuli to subject 410. As described above, display device may comprise any type of display device instead of or in addition to the illustrated monitor 420, such as monitors, screens, goggles, or any other device or apparatus that may provide visual stimuli to be perceived by subject 410.

Any number of sports related scenarios may be presented as a visual stimuli to an individual and imaged by the individual to provide data, such as stability data and eye movement data. For example, a soccer goal keeper may improve her/his performance as a result of a comparison of stability and/or eye movement data while being presented with the visual stimulus of an approaching shot ball to be saved (real or simulated) with data collected while the goal keeper images the shot. By way of further example, a basketball guard may benefit from utilizing the present invention in the scenario of bringing a ball across midcourt, evaluating the positions and movements of other players, and making a pass—for example, to evaluate whether the guard may be tipping the defense to the pass by looking or leaning to the destination of the pass prematurely. Of course, any type of scenario may be used in accordance with the present invention whether common in a sport, rare in a sport, unheard of in a sport, or contrived entirely for purposes of testing.

Control unit 440 may comprise any type of computing device executing software causing it to operate in accordance with the present invention. Control unit 440 may communicate using one or more wireless links 441 with display device, such as monitor 420, and the various data collection devices, such as those described above. Wireless links 441 may use any wireless communication protocol, such as Bluetooth, and different devices may use different wireless communication protocols. One of ordinary skill in the art will appreciate, of course, that cables, wires, or any other type of link may be used to permit communication between test unit 440 and the various devices used to collect data or to display stimuli in accordance with the present invention. Different types of connections may be used for different devices or displays.

Control unit 440 may operate to collect data from data collection devices regarding the performance of subject 410 with no visual stimuli provided on display 420, with a visual stimuli provided on display 420, and/or while subject 410 visualizes visual stimuli. Control unit 440 may analyze the data collected by some or all of the data collection devices. For example, data may be analyzed by comparing data collected during different periods of time. Alternatively (or additionally), collected data by be transmitted from control unit 440 to a server 442 or other remote device over link 443 or any other type of connection for analysis. Server 442 or other remote device may be located at any place, and may be distant from control unit 440. Server 442 may perform a comparison and/or other analysis of collected data instead of or in addition to control unit 440. The collected data and/or the analysis of the collected data may be presented to a trainer, coach, medical professional, other third party assisting in testing and/or training subject 410, or even subject 410 himself/herself. The collected data, the comparison of the collected data, an/or other analysis of the collected data may be presented in a variety of forms, such as in numerical form or in a graphical form, and may be presented using any of a variety of output devices. Examples of output devices include, but are not limited to, output monitor 444 operably connected to control unit 440 by connection 445, printer 446 operably connected to control unit 440 by connection 447, and monitor 420 (or any other display device) operably connected to control unit 440 by wireless link 441. Further, the collected data and/or analysis of collected data may be stored on any type of storage media (not shown) for subsequent display and/or analysis. Storage media may comprise, for example, hard drives, flash drives, compact discs, dvds, floppy discs, tape drives, or any other type of storage media. Storage media may be located at control unit 440, server 442, or any other location, and may be a separate device, integral to another device, or detachably attached to another device.

Figure 5:
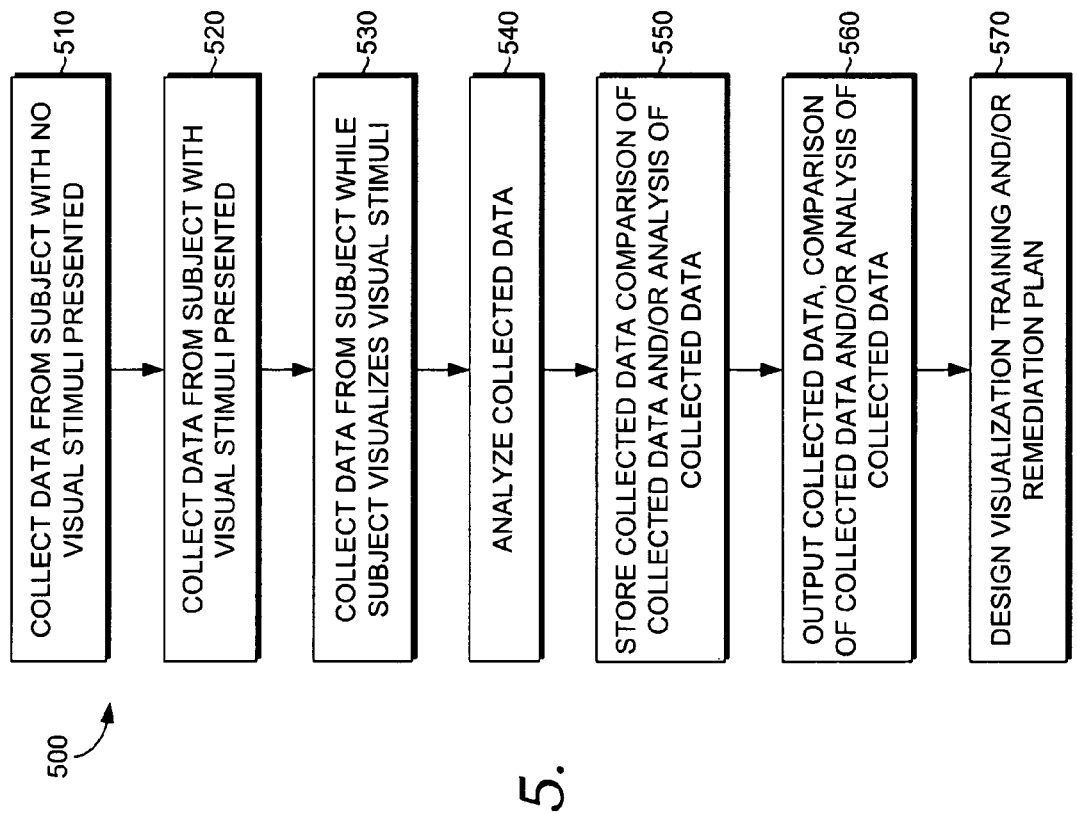
FIG. 5 illustrates a further method for testing and/or training the visualization abilities of an individual in accordance with the present invention.

Referring now to FIG. 5, a method 500 for testing and/or training the visual and/or visualization abilities of a subject is illustrated. In step 510, performance data is collected from a subject with no visual stimuli presented for a period of time. Optionally, step 510 may be performed after a subject has engaged in an exercise to clear thoughts, images, and the like from the subject's mind. In step 520, performance data is collected from a subject with visual stimuli presented for a period of time. The strength of the visual stimuli presented in step 520 may vary. In step 530, performance data is collected from a subject while the subject visualizes a visual stimuli for a period of time. In step 530, visual stimuli may be presented to subject, for example to increase the difficulty of visualization for subject, or, alternatively, no visual stimuli may be presented to subject to avoid distracting subject from visualization. Method 500 may be iteratively repeated any number of times. If method 500 is iteratively repeated, the complexity and/or strength of visual stimuli presented in step 520 may vary based upon performance data collected in step 510, step 520, and/or step 530 of iterations of method 500. The performance data collected in step 510, step 520, and/or step 530 may be, for example, stability data, physiological data, eye movement data, and/or any other type of data, such as described herein. If the steps of collecting performance data with visual stimuli presented are followed by steps of collecting performance data with no visual stimuli presented, or vice versa, the visual stimuli may be presented and/or removed gradually, so as to avoid a startle reflex reaction from the subject, or suddenly, so as to increase the difficulty of testing and/or training for the subject. Method 500 may additionally/alternatively utilize delays between performance data collection in step 510, step 520, and/or step 530 to, for example, avoid collecting data from the subject during transitory periods.

In step 540, the collected performance data is analyzed, which may comprise comparing the performance data collected in step 510, step 520, and/or step 530 to identify differences that may be indicative of strengths and/or weaknesses of an individual's visual and/or visualization abilities. The analysis of step 540 may comprise a comparison of the different types of collected performance data, which may indicate whether a given subject's visual and/or visualization skills may be improved, or provide feedback regarding the training of those skills by subject. In step 550 the performance data collected and/or the analysis of the collected performance data may be stored. Any type of storage media may be used in step 550, and the storage media used in step 550 may be located proximate or remote to the subject during testing/training. In step 560 the collected performance data, comparison of collected performance data, and/or other analysis of collected performance data may be output. Step 560 may utilize any type of output device and the output may be in any format. In step 570 a visualization training and/or remediation plan may be developed. Step 560 may be performed by an individual (such as a trainer, coach, medical profession, the subject himself/herself, etc.), a computing device, or any combination of individuals and/or computing devices.

Figure 6:
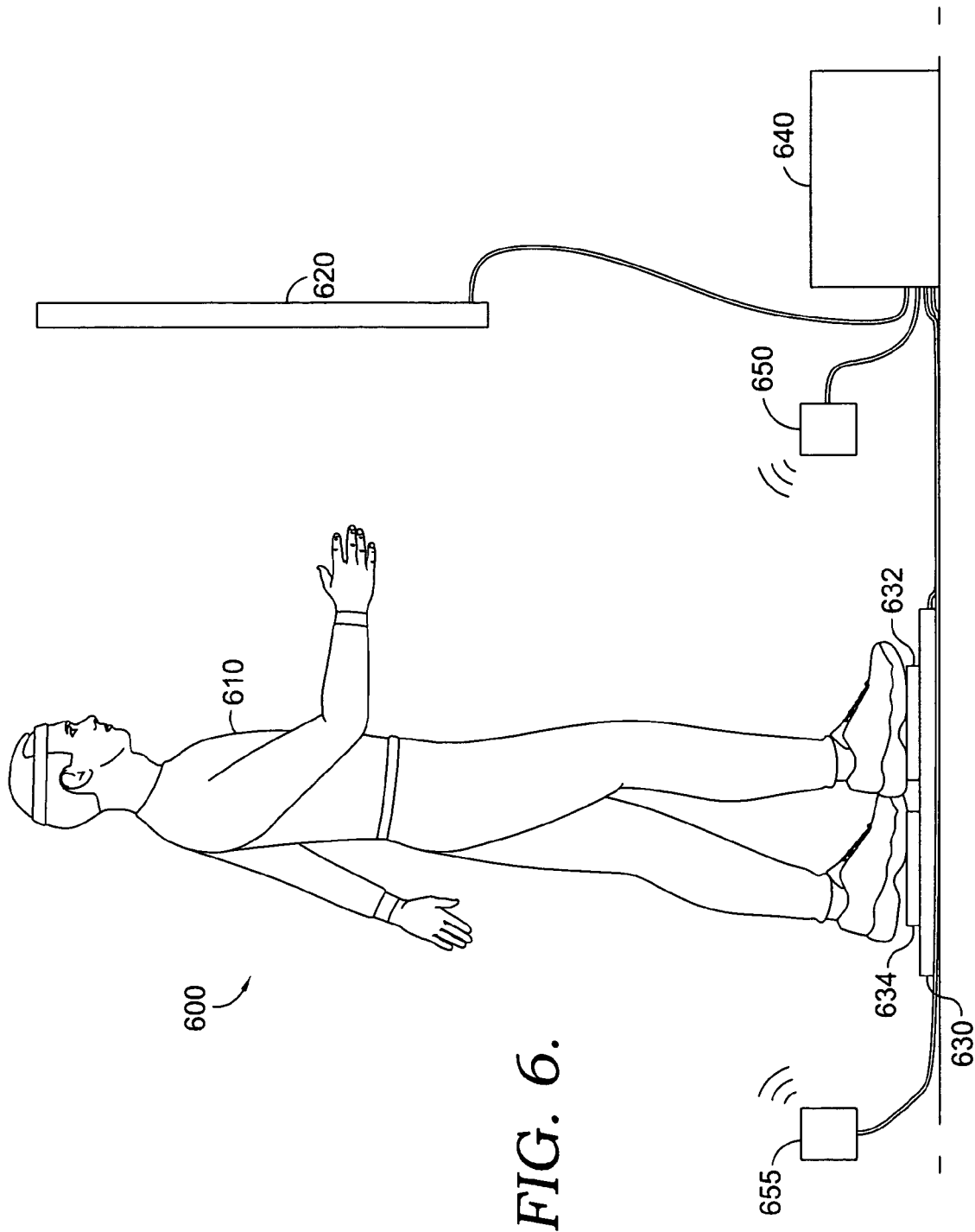
FIG. 6 illustrates a further system for testing and/or training the visualization abilities of an individual in accordance with the present invention.

Referring now to FIG. 6, a further system 600 in accordance with the present invention is illustrated. System 600 may be used to test and/or train the visual and/or visualization abilities of subject 610. While system 600 may utilize any of the performance data collection devices described above to collect stability data, physiological data, eye movement data, and/or any other type of data, system 600 is shown with a platform 630, a first pressure sensitive plate 632, and a second pressure sensitive plate 634 to collect stability data from subject 610. System 600 may further comprise a monitor 620 as a display device. Display device, as described more fully above, may be any type of monitor, screen, goggle, or other display device. Test unit 640 may comprise any type of computing device executing software causing it to operate in accordance with the present invention. Test unit 640 may coordinate the display of visual stimuli on display device, such as monitor 620, and the collection of data, such as stability data, using data collection devices, such as platform 630, first pressure sensitive plate 632, and/or second pressure sensitive plate 634.

System 600 may provide secondary stimuli to subject 610 using one or more secondary output devices such as, for example, a first speaker 650 and/or a second speaker 655. Secondary stimuli may be, for example, sounds, physical sensations, additional visual stimuli such as bright lights, smells, or any other secondary stimuli that may be provided to subject 610. For example, a secondary stimuli of a sound may be provided to subject 610 to obtain additional data regarding the performance of subject 610 during visual and/or visualization processes. A secondary stimuli may serve solely as a distraction to subject 610, or may require an additional input by subject via an user operable input device, such as the depression of a button, a verbal response detected by a voice recognition system, a gesture detected by a gesture recognition system, or any other physical response received by an input device. The responses by a subject to secondary stimuli, and/or whether a response is appropriate, may be collected as part of stability, physiological, or other data collected by system 600.

The appropriate response to a secondary stimulus provided by system 600 may depend upon the stimulus itself. For example, subject 610 may be instructed to lean toward the direction from which a sound originates, and/or to respond to only certain sounds and not to respond to other sounds. Secondary stimuli in addition to sound, as illustrated in FIG. 6, may be provided by, for example, tilting the platform 630, first pressure sensitive plate 632, and/or second pressure sensitive plate 634, by blowing air upon subject 610, by contacting subject 610 with various physical devices, by flashing lights perceivable by subject 610, by generating odors perceivable by subject 610 or by generating any other kind of stimulus perceivable by subject 610. A secondary stimulus may be provided while no visual stimulus is presented to the subject 610, while a visual stimulus is provided to subject 610, and/or while subject 610 is visualizing a visual stimulus. Display devices, data collection devices, output devices, input devices, secondary stimuli output devices, storage devices, computing devices, and connections between the various components in accordance with the present invention may vary from those illustrated in FIG. 6.

Figure 7:
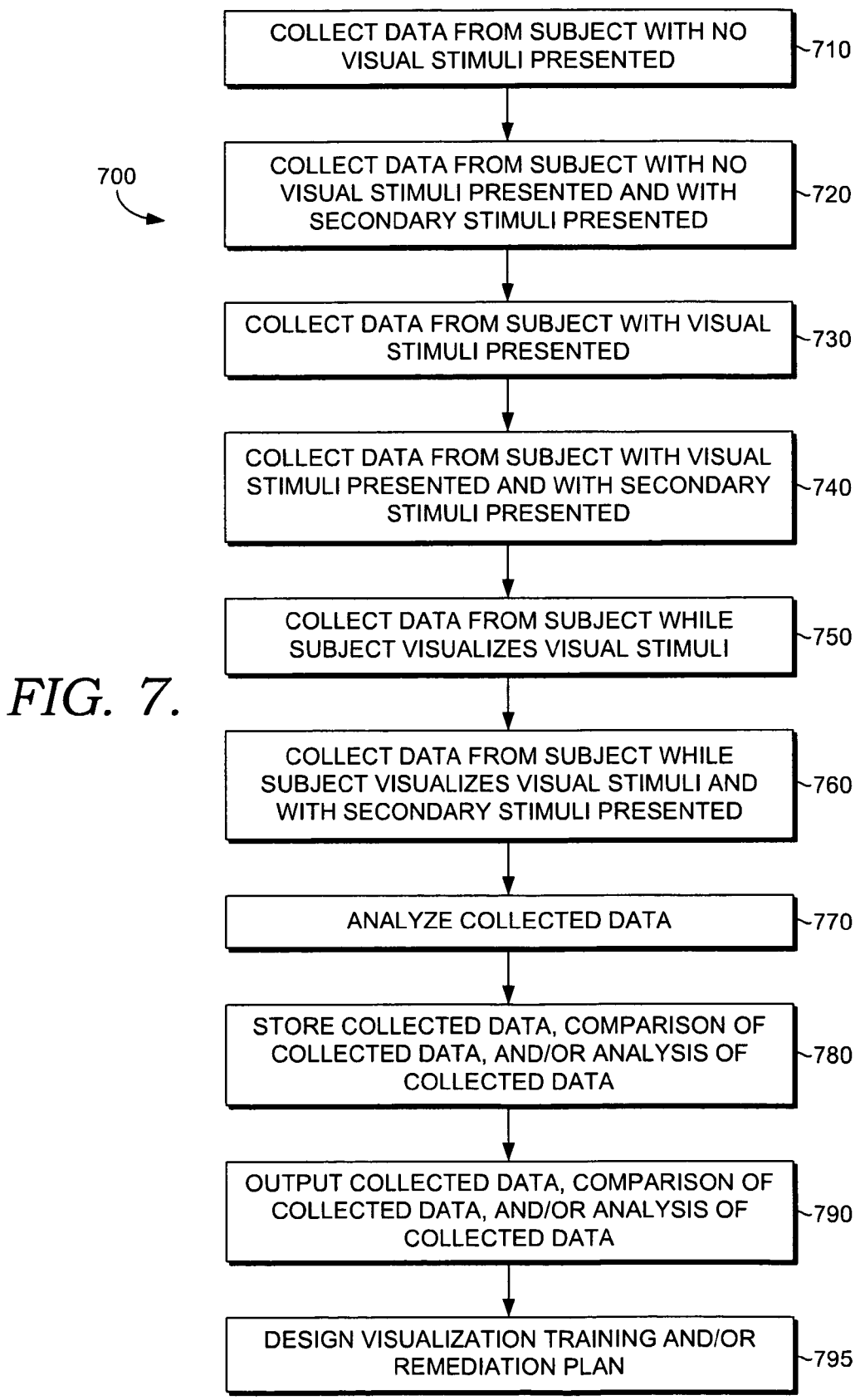
FIG. 7 illustrates a further method for testing and/or training the visualization abilities of an individual in accordance with the present invention.

Referring now to FIG. 7, a further method 700 for testing and/or training the visualization abilities of an individual in accordance with the present invention is illustrated. In step 710, performance data is collected from a subject with no visual stimuli presented for a period of time. Optionally, step 710 may be performed after a subject has engaged in an exercise to clear thoughts, images, and the like from the subject's mind. In step 720, performance data is collected from a subject with no visual stimuli presented for a period of time and with a secondary stimuli presented for a least a portion of the period of time. In step 730, performance data is collected from the subject with visual stimuli presented for a period of time. In step 740, performance data is collected from a subject with visual stimuli presented for a period of time and with a secondary stimuli presented for at least a portion of the period of time. In step 750, performance data is collected from a subject while the subject visualizes a visual stimuli for a period of time. In step 760, performance data is collected from a subject while the subject visualizes visual stimuli for a period of time and with secondary stimuli presented for at least a portion of the period of time. The performance data collected in step 710, step 720, step 730, step 740, step 750, and/or step 760 may include any type of stability data, physiological data, eye movement data, response to stimuli using one or more user operable input device, and/or other type of data, such as the types of data described elsewhere herein. In steps of collecting performance data with visual stimuli presented are followed by steps of collecting performance data with no visual stimuli presented, or vice versa, the visual stimuli may be presented and/or removed gradually so as to avoid a startle reflex reaction from the subject, or suddenly, so as to increase the difficulty of training and/or testing for the subject. Method 700 may additionally/alternatively utilize delays between data collection steps to, for example, avoid collecting data during transitory periods.

In step 770, the collected performance data may be analyzed. The analysis of step 770 may comprise, for example, a comparison of the collected performance data from different periods of time and/or portions of periods of time to identify relative strengths and/or weaknesses of an individual's visual and/or visualization skills. The analysis of step 770 may be used to adjust the complexity and/or strength of visual stimuli presented in subsequent iterations of method 700. In step 780 the performance data collected and/or the analysis of collected performance data may be stored. Any type of storage media may be used in step 780. In step 790 the collected performance data and/or analysis of collected performance data may be output. Step 790 may utilize any type of output device and the output may be in any format. In step 795 a visualization training and/or remediation plan may be designed by an individual (such as a trainer, coach, medical professional, the subject himself/herself, etc.), a computing device, or any combination of individuals and/or computing devices. A visualization training and/or remediation plan may include devices and/or training to improve the visual abilities of an individual. Further, a visualization training and/or remediation plan may include visualization tasks of increasing difficulty and/or complexity. Of course, the steps of method 700 may be performed in varying orders, a varying number of times, and may be partially or entirely omitted.

Figure 8:
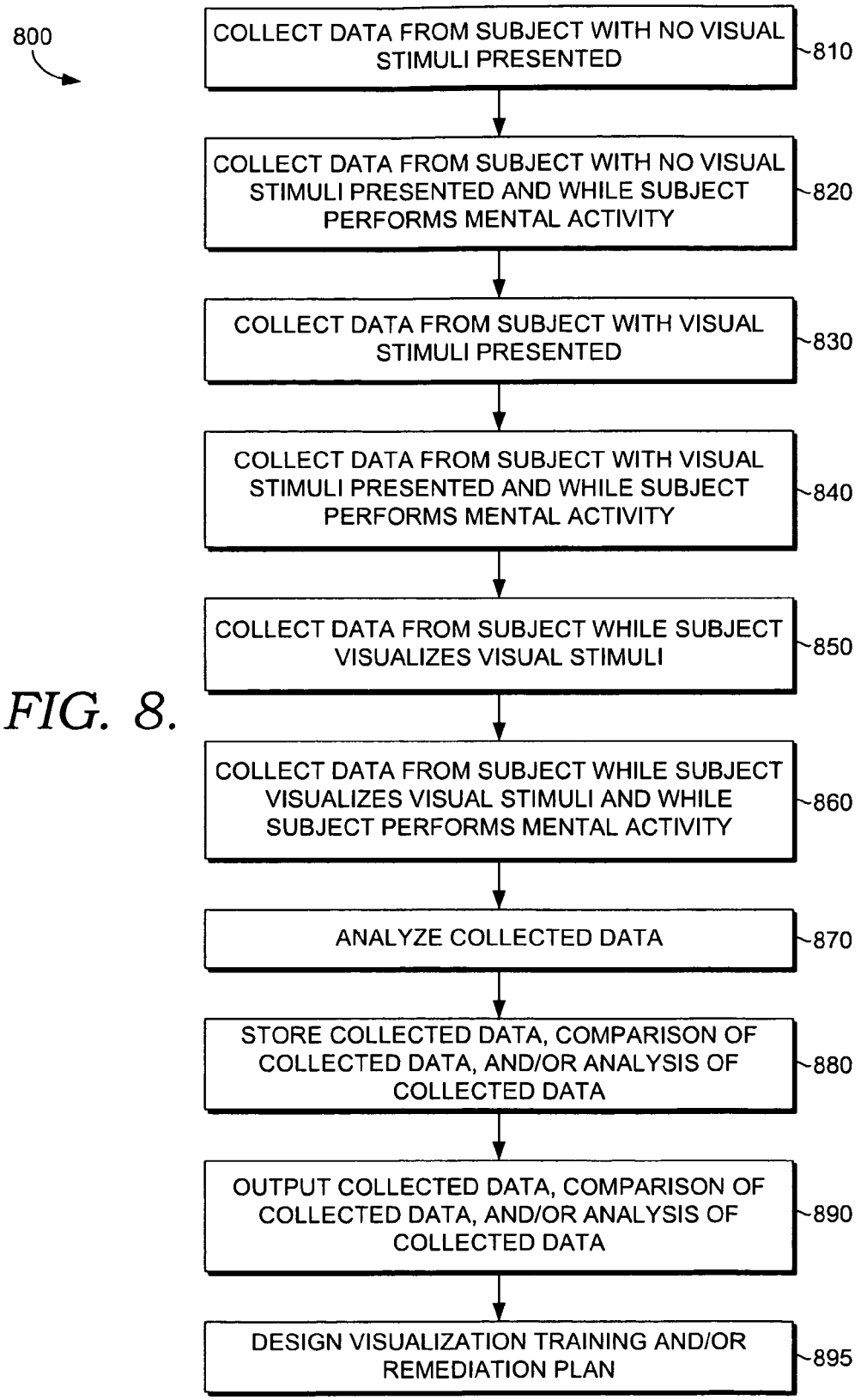
FIG. 8 illustrates a further method for testing and/or training the visualization abilities of an individual in accordance with the present invention.

Referring now to FIG. 8, a further method 800 for testing and/or training the visualization skills of an individual in accordance with the present invention is illustrated. In step 810, performance data may be collected from a subject with no visual stimuli presented for a period of time. Optionally, step 810 may be performed after a subject has engaged in an exercise to clear thoughts, images, and the like from the subject's mind. In step 820, performance data may be collected from a subject with no visual stimuli presented for a period of time while the subject performs a mental activity for at least a portion of the period of time. In step 830, performance data may be collected from subject with a visual stimuli presented for a period of time. In step 840, performance data may be collected from a subject with visual stimuli presented for a period of time while the subject performs a mental activity for at least a portion of the period of time. In step 850, performance data may be collected from a subject while the subject visualizes visual stimuli for a period of time. In step 860, performance data may be collected from a subject while the subject visualizes visual stimuli for a period of time and performs a mental activity for at least a portion of the period of time. The mental activity or activities performed in step 820, step 840 and/or step 860 may be, for example, solving math problems answering questions, or any other activity requiring mental effort from the subject. If steps of collecting performance data with visual stimuli presented are followed by steps of collecting performance data with no visual stimuli presented, or vice versa, the visual stimuli may be presented and/or removed gradually so as to avoid a startle reflex reaction from the subject, or suddenly, so as to increase the difficulty of training and/or testing. Method 800 may additionally/alternatively utilize delays between performance data collection steps to avoid collecting performance data from subject during transitory periods.

The performance data collected in step 810, step 820, step 830, step 840, step 850, and/or step 860 may be, for example, stability data, physiological data, eye movement data, the results of the mental activity (such as solutions to math problems or answers to questions), inputs by a subject using one or more user operable input device, and/or any other type of data, such as described elsewhere herein. In step 870, the collected data may be analyzed. The analysis of step 870 may comprise, for example, a comparison of performance data collected during different periods of time or portions of periods of time. A mental activity as used in steps 820, 840, and 860 may be any activity requiring additional mental processing by a subject beyond perceiving and/or visualizing a visual stimuli. For example, a subject may be instructed to count backwards from a given starting point, perform arithmetic problems, answer questions regarding any manner of topic, or otherwise engage in mental activities as part of steps 820, 840, and 860.

In step 880 the performance data collected and/or the analysis of the collected data may be stored. Any type of storage media may be used in step 880. The analysis of step 880 may be used to adjust the complexity and/or strength of visual stimuli presented in subsequent iterations of method 800. In step 890 the collected performance data and/or the analysis of the collected performance data may be output. Step 890 may utilize any type of output device and the output may be in any format. In step 895 a visualization training and/or remediation plan may be designed by an individual (such as a trainer, coach, medical professional, the subject himself/herself etc.), a computing device, or any combination of individuals and/or computing devices. A visualization training and/or remediation plan may include devices and/or training to improve the visual abilities of an individual. Further, a visualization training and/or remediation plan may include visualization tasks of increasing difficulty and/or complexity.

Numerous variations may be made to the systems and methods illustrated in the figures and discussed herein. For example, any type of data may be collected regarding the performance of a subject during testing and/or training. The types of data collected, and the devices and apparatuses used to collected that data need not be limited to those described herein. Moreover, steps in the methods described herein may be omitted without departing from the scope of the present invention. For example, steps such as collecting performance data without presenting visual stimuli may be omitted without departing from the scope of the present invention. Additionally, the steps of the various methods described herein may be performed in different orders without departing from the scope of the present invention. Further, steps from the various methods described herein may be combined in a single method. For example, the use of secondary stimuli in method 700 and the use of a mental activity in method 800 may be combined. Similarly, the components of the various systems described herein may be combined to form systems beyond those described herein. One will also realize that a test unit as described herein may comprise one or more devices. For example, data may be collected separately for one or more of the measurements made of subject during testing and/or training, and that data may later be used either by inputting it into a computer or other device or by evaluating by a trainer or clinician. These and other variations will be well understood by one of ordinary skill in the art.

The invention claimed is:

1. A system for testing or training the stability of an individual, the system comprising:
   a display device that provides visual stimuli to the individual for a first period of time;
   at least one stability measurement device that measures the balance of the individual; and
   a control unit coupled to the at least one stability measurement device configured to:
   (1) collect a first set of measurement data while the display device provides the visual stimuli to the individual for the first period of time,
   (2) prevent the individual from being exposed to the visual stimuli and collect a second set of measurement data while the individual is instructed to form a mental image of the visual stimuli, the second set of measurement data collected during a second period of time not coextensive with the first period of time, and
   (3) compare the first set of measurement data to the second set of measurement data to evaluate the individual.

2. The system for testing or training the stability of an individual of claim 1, wherein the at least one stability measurement device comprises at least one pressure sensitive surface stood upon by the individual during the first period of time and the second period of time.

3. The system for testing or training the stability of an individual of claim 1, wherein the at least one stability measurement device comprises a plurality of inertial sensors that are affixed to the individual during the first period of time and the second period of time.

4. The system for testing or training the stability of an individual of claim 1, wherein the second period of time occurs after the first period of time.

5. The system for testing or training the stability of an individual of claim 4, wherein the at least one stability measurement device and control unit is further configured to:
   measure the stability of the individual during a third period of time not coextensive with the first period of time and not coextensive with the second period of time, wherein the third period of time occurs before the first period of time, and wherein the display device does not provide the visual stimuli to the individual during the third period of time; and
   compare the first, second and third set of measurement data to evaluate the individvual.

6. The system for testing or training the stability of an individual of claim 1, wherein the display device comprises a display screen.

7. The system for testing or training the stability of an individual of claim 1, wherein the display device comprises display goggles.

8. The system for testing or training the stability of an individual of claim 1, wherein the visual stimuli displayed by the display device simulates an activity.

9. A computerized method stored on a non-transient storage medium carried out by a visualization training system having at least one processor for testing or training the visualization ability of an individual, the method comprising:
   measuring performance of the individual while the individual is exposed to a first set of visual stimuli by a display device to obtain a first set of performance data;
   preventing the individual from being exposed to the first set of visual stimuli and measuring performance of the individual while the individual is instructed to form a mental image of the first set of visual stimuli to obtain a second set of performance data; and
   comparing, using the at least one processor, the first set of performance data and the second set of performance data to evaluate the visualization ability of the individual.

10. The method for testing or training the visualization of an individual of claim 9, wherein the performance data comprises stability data.

11. The method for testing or training the visualization of an individual of claim 9, wherein the performance data comprises eye movement data.

12. The method for testing or training the visualization of an individual of claim 9, wherein the performance data comprises physiological data.

13. The method for testing or training the visualization of an individual of claim 9, wherein the performance data comprises stability data and eye movement data.

14. The method for testing or training the visualization of an individual of claim 9, wherein the performance data comprises stability data and physiological data.

15. The method for testing or training the visualization of an individual of claim 9, wherein the performance data comprises eye movement data and physiological data.

16. The method for testing or training the visualization of an individual of claim 9, wherein the performance data comprises stability data, eye movement data, and physiological data.

17. The method for testing or training the visualization of an individual of claim 9, wherein the display device used to expose the individual to visual stimuli comprises a display screen.

18. The method for testing or training the visualization of an individual of claim 9, wherein the display device used to expose the individual to visual stimuli comprises display goggles.

19. The method for testing or training the visualization of an individual of claim 9, wherein the visual stimuli to which the individual is exposed comprises simulated activity.

20. The method for testing or training the visualization of an individual of claim 9, wherein measuring the performance of the individual comprises using at least one pressure sensitive surface upon which the individual stands to detect the pressure exerted by the individual while standing.

21. The method for testing or training the visualization of an individual of claim 9, wherein measuring the performance of the individual comprises using at least one inertial sensor affixed to the individual to measure the movement of the individual while standing.

22. The method for testing or training the visualization of an individual of claim 9, wherein measuring the performance of the individual comprises using an eye movement monitoring system to detect the eye movements of the individual.

23. The method for testing or training the visualization of an individual of claim 9, wherein measuring the performance of the individual comprises using an electro-oculogram to detect the eye movements of the individual.

\* \* \* \* \*